United States Patent [19]

Clark, Jr.

[11] Patent Number: 4,721,677

[45] Date of Patent: Jan. 26, 1988

[54] IMPLANTABLE GAS-CONTAINING BIOSENSOR AND METHOD FOR MEASURING AN ANALYTE SUCH AS GLUCOSE

[75] Inventor: Leland C. Clark, Jr., Cincinnati, Ohio

[73] Assignee: Children's Hospital Medical Center, Cincinnati, Ohio

[21] Appl. No.: 47,013

[22] Filed: May 7, 1987

Related U.S. Application Data

[62] Division of Ser. No. 777,234, Sep. 18, 1985, Pat. No. 4,680,268.

[51] Int. Cl.[4] ............................................. C12M 1/34
[52] U.S. Cl. .................................... 435/291; 128/635; 204/403; 204/415; 435/288
[58] Field of Search ................ 128/635; 204/403, 415; 435/288, 291, 808, 817

[56] References Cited

U.S. PATENT DOCUMENTS

| | | | |
|---|---|---|---|
| 2,913,386 | 11/1959 | Clark, Jr. | 204/415 |
| 3,380,905 | 4/1968 | Clark, Jr. | 204/415 |
| 3,539,455 | 11/1970 | Clark, Jr. | 204/1 T |
| 3,577,332 | 5/1971 | Porter et al. | 204/408 |
| 3,591,480 | 7/1971 | Neff et al. | 435/288 X |
| 3,911,138 | 10/1975 | Clark, Jr. | 514/746 |
| 3,992,158 | 11/1976 | Przybylowicz et al. | 422/57 |
| 4,040,908 | 8/1977 | Clark, Jr. | 435/11 |
| 4,151,845 | 5/1979 | Clamens | 128/214 E |
| 4,240,889 | 12/1980 | Yoda et al. | 435/288 X |
| 4,245,634 | 1/1981 | Albisser et al. | 128/213 R |
| 4,313,439 | 2/1982 | Babb et al. | 128/214 F |
| 4,368,737 | 1/1983 | Ash | 604/175 |
| 4,374,013 | 2/1983 | Enfors | 204/1 T X |
| 4,378,016 | 3/1983 | Loeb | 128/260 |
| 4,388,166 | 6/1983 | Suzuki et al. | 204/403 |
| 4,402,694 | 9/1983 | Ash et al. | 604/891 |
| 4,403,984 | 9/1983 | Ash et al. | 604/50 |
| 4,443,480 | 4/1984 | Clark, Jr. | 424/352 |
| 4,458,686 | 7/1984 | Clark, Jr. | 128/635 |
| 4,464,230 | 8/1984 | Langdon | 204/1 T |
| 4,484,987 | 11/1984 | Gough | 204/1 T |

OTHER PUBLICATIONS

L. C. Clark, Jr.: Electrode Systems for Continuous Monitoring in Cardiovascular Surgery, Annals New York Academy of Sciences, vol. 102, Article 1, pp. 29–45, Oct. 31, 1962.

L. C. Clark, Jr. et al: Rapid Electroenzymatic Measurement of Lactate in Microsamples of Spinal Fluid, Clinical Biochemistry, vol. 17, Oct. 1984.

S. Kaplan et al: Intravascular Polarographic and Potentiometric Electrodes, Intravascular Catheterization, Chapter 10, pp. 583–605.

M. Shichiri et al: Glycaemic Control in Pancreatectomized Dogs with a Wearable Artificial Endocrine Pancreas, Diabetologia (1983) 24: 179–184.

L. C. Clark, Jr. et al: Continuous Recording of Blood Oxygen Tensions by Polarography, J. Appl. Physiol., 6(3), 189–193 (1953).

(List continued on next page.)

Primary Examiner—Samuel Scott
Assistant Examiner—Allen J. Flanigan
Attorney, Agent, or Firm—Wood, Herron & Evans

[57] ABSTRACT

The present invention relates to a novel implantable biosensor and method for sensing products, such as hydrogen peroxide, generated from an enzymatic reaction between an analyte, like glucose, and an enzyme in the presence of oxygen. The novel implantable biosensor is uniquely equipped with an enclosed chamber for containing oxygen and can be adapted for extracting oxygen from animal tissue adjacent the container. The reservoir of oxygen contained in the enclosed chamber is supplied to the enzymatic reaction from both sides of a membrane. The enclosed chamber is uniquely designed to be impermeable to substances, like liquid and cells, that possibly can interfere with the supply of the oxygen permeating through the membrane to the enzymatic reaction. Also, the implantable biosensor is designed to optically or electrically sense products generated from the enzymatic reaction which serve as a function of the analyte.

28 Claims, 4 Drawing Figures

OTHER PUBLICATIONS

S. Kaplan et al: Shunt Detection with Hydrogen, Ascorbate and Oxygen Electrodes, Intravascular Catheterization, pp. 1-24, 1977.

Wise Young, H2 Clearance Measurement of Blood Flow: A Review of Technique and Polarographic Principles, Stroke vol. 11, No. 5, Sep.-Oct. 1980.

L. C. Clark, Jr. et al: Theoretical and Practical Bases for Implantable Glucose Sensors with Special Reference to the Peritoneum, Proceedings of the Symposium on Biosensors, Sep. 1984.

A. M. Albisser: Insulin Delivery Systems: Do They Need a Glucose Sensor?, Diabetes Care, vol. 5, No. 3, May-Jun. 1982.

I. Fatt et al: Its Theory of Operation and Its Application in Biology, Medicine, and Technology, Polarographic Oxygen Sensor.

D. R. Thevenot: Problems in Adapting a Glucose-Oxidase Electro-Chemical Sensor into an Implantable Glucose-Sensing Device, Diabetes Care, vol. 5, No. 3, May-Jun. 1982.

L. C. Clark, Jr. et al: Rapid Micromeasurement of Lactate in Whole Blood, Critical Care Medicine, vol. 12, No. 5, 461-464.

L. C. Clark, Jr. et al: Implanted Electroenzymatic Glucose Sensors, Diabetes Care, vol. 5, No. 3, May-Jun. 1982.

IMPLANTABLE GAS-CONTAINING BIOSENSOR AND METHOD FOR MEASURING AN ANALYTE SUCH AS GLUCOSE

This is a division of application Ser. No. 777,234 filed Sept. 18, 1985 now U.S. Pat. No. 4,680,268.

BACKGROUND OF THE DISCLOSURE

Considerable effort over the years has been devoted to discovering and improving analytical techniques for measuring biological substances in connection with medical and industrial applications. An example of one such technique developed concerned polarographic electrode systems which wer used to measure various biological materials qualitatively and quantitatively, and reference is made to my earlier U.S. Pat. No. 2,913,386 describing such a polarographic electrode system for the measurement of oxygen and the like. Reference is also made to my U.S. Pat. No. 3,380,905 which pertains to an improvement of the polarographic electrode system described in the above-mentioned U.S. patent.

About twenty years ago, enzyme-coupled electrodes were reported for the polarographic analysis of biological substances. For example, in my U.S. Pat. Nos. 3,539,455 and 3,913,386, membrane polarographic electrode systems and methods were described for the rapid and accurate quantitative analysis of biological substances which theretofore could not be analyzed directly by polarographic methods. According to the description in my U.S. Pat. No. 3,539,455, small molecular substances, such as glucose, were measured with a membrane polarographic electrode system. By use of cellulose or another membrane which is permeable to small molecules, such as glucose, but is impermeable to proteins, the membrane kept glucose oxidase enzyme on the side of the membrane with the anode for reaction with glucose. Therefore, for example, if a sample of blood were placed on the membrane side opposite the electrode, with an aqueous solution of the enzyme and oxygen on the electrode side of the membrane, the low molecular weight materials, such as glucose, passed from the blood samples through the membrane for enzymatic reaction adjacent the electrode. After a certain period of time a steady state was reached when the hydrogen peroxide concentration was directly proportional to the glucose concentration and the cell produced a current flow as a function of the amount of hydrogen peroxide being formed which served as an indication of the amount of glucose present. As disclosed in my article entitled "Electrode Systems for Continuous Monitoring in Cardiovascular Surgery", *N.Y. Acad. of Sciences.* 102:29-45 (1962), the Clark oxygen electrode could be arranged so that it was sensitive to glucose by virtue of the fact that oxygen was consumed by enzymatic reaction in proportion to glucose content. In such arrangement, the inner membrane was impermeable to glucose and the reaction was monitored by the drop in oxygen. My early membrane polarographic techniques for measurement of hydrogen peroxide were limited to the detection of small molecules which were capable of permeating the membrane for enzymatic reaction with an enzyme being contained on the electrode side of the membrane.

More recently, enzymatic techniques for measuring macromolecules, such as cholesterol have been made. Generally, the enzymatic methods combined two enzymes, cholesterol oxidase and cholesterol ester hydrolase, with colorimetric techniques. These colorimetric methods relied on enzymatic conversion of cholesterol or its esters to cholestenone and hydrogen peroxide, and then on the reaction of the hydrogen peroxide with various compounds to produce measurable chromagens and fluorogens. In my U.S. Pat. No. 4,040,908, I described a membrane polarographic anode suitable for measuring macromolecular substances, such as cholesterol, utilizing enzymatic reactions as a means to measure such macromolecular substances.

Additional techniques have been developed for measuring other biological substances in blood. For instance, ethanol is currently measured in blood either directly or by breath sampling, by classical chemical, gas chromatographic and enzyme methods. One of the alcohol enzyme methods, for example, depends upon the polarographic measurement of hydrogen peroxide, while others depend upon the consumption of oxygen. In my more recent U.S. Pat. No. 4,458,686, I disclosed the use of a polarographic electrode as a skin-contact analyzer to transcutaneously measure oxygen for determining blood substances, such as glucose or alcohol as well as measurement of alcohol going through the skin.

One of the most important biological substances is glucose. This is true because glucose plays such a major role in the metabolism of the body in health and disease, particularly diabetes. For instance, most of the scientific evidence to date indicates that it is the high blood and tissue glucose concentration per se, and not too low an insulin level or the presence of abnormal metabolites, such as hydroxybutyric acid and the like, which causes the organ damage in the various forms of diabetes mellitus. This damage may be caused by glycylation of many of the tens of thousands of proteins in the body. Such glycylation is reflected by the glucosehemoglobin AlC level in the blood, a substance commonly measured to give a time-integrated level for blood glucose. Since all enzymes are proteins, the high glucose level probably impairs the catalytic functions in every part of the body. Typical serious damage related to diabetes is blindness, loss of limbs, cardiac and circulatory failure and death.

At present, insulin is administered either by injecting intermittently throughout the day to control blood glucose or, in a very small population of diabetics, by a programmable pump which injects insulin subcutaneously. This results in considerable, potentially dangerous, fluctuation in blood glucose depending upon the severity of the disease. In some forms of diabetes the Beta cells which make insulin are completely destroyed and the person becomes totally insulin dependent for survival.

In view of the above background, it would be desirable to have a device which is capable of continuously sensing glucose in the blood of diabetic patients so that the insulin or glucose can be more effectively administered and regulated. Extensive efforts heretofore have been directed toward developing an implantable glucose sensor having the capability of controlling an insulin pump or at least to provide a continuous signal reflecting blood glucose concentrations. However, it is widely believed that an implanted enzyme-based glucose sensor cannot work or, if it does work, such a sensor would last at best for only a few days, after implantation in the blood or a body cavity. In Schichiri, M. et al: Glycaemic Control in Pancreatectomized Dogs with a Wearable Artificial Endocrine Pancreas, *Diabetologia.* 24:179–184 (1983), it was reported that a glucose sensor was implanted and it lasted for six days after the date of in vivo implantation. Up to this point, such success even though limited has been considered remarkable. Nevertheless, the limited operability of such sensors lead the scientific community to believe that implanted glucose oxidase type glucose sensors are not practical. In support of such belief, a penumbra of reasons are given. For instance, it is generally thought that the enzyme, glucose oxidase, is too unstable to remain active for any period of time in a human at human body temperature. Furthermore, it is believed that glucose oxidase would be destroyed by bacteria or fungi. It is further believed that the electrodes' permeable membrane would be destroyed by tissue cells and enzymes or would become plugged as a result of large molecules, cellular debris and white and red blood cells collecting thereon. Additionally, it is thought that the amount of oxygen available necessary for the enzymatic reaction would be insufficient; or that co-enzymes would diffuse away from the enzyme through glucose permeable membranes; or that the platinum electrode surface would become plated, poisoned, inactivated or passivated thereby preventing reduction of the hydrogen peroxide generated; or that tissue response would interfere with glucose permeation through the membrane.

In summary, while there are a variety of devices and techniques available for the measurement of biological substances, new implantable devices and methods are needed for the measurement, administration and/or regulation of key biological substances, such as blood glucose and insulin. It would be especially beneficial if a satisfactory implantable device could be provided to aid in the control and alleviation of diabetes.

SUMMARY OF THE INVENTION

In brief, the present invention seeks to alleviate the above discussed problems and shortcomings of the present state of the art. This invention is directed to new and improved optical, electrical or other devices for sensing a product or reactant, such as hydrogen peroxide, derived from enzymatic reactions between analytes and enzymes as a measure of the amount of the analytes. This invention is predicated in part upon the discovery that problems heretofore associated with enzyme sensors can be overcome by providing a structure for an ample and/or steady supply of oxygen for enzymatic reaction at the sensor surface. The device of this invention is also uniquely suited for in vivo implantation and in measuring analytes, such as glucose, in undiluted, whole blood. It has been discovered that an enzyme and an electrode of this device when implanted does in fact remain active for as long as six months or more. In view of the present state of the art, this is remarkable. In one preferred form of the invention, the amount or level of hydrogen peroxide is detected as a measure of the amount or level of glucose in the animal body. The types of animal fluid or tissue selected for implantation include both blood and nonblood sites such as intravascular, spinal fluid, peritoneal fluid, and extra and intracellular fluids.

In one embodiment of the present invention, the device comprises a gas permeable membrane having opposed sides, an enzyme on one side of the membrane for enzymatic reaction with the analyte in the presence of molecular oxygen to generate a product, a closed container for the molecular oxygen on the opposite side of the membrane to supply molecular oxygen through the membrane for the enzymatic reaction, and means for sensing the generated product or a reactant which functions as a measure of the analyte.

The present invention contemplates providing sensing devices predicated upon sensing a product or reactant involved in an oxygen-dependent enzymatic reaction and having the capability to provide to the enzymatic reaction from the container located on the side of the membrane opposite the enzyme a steady source of oxygen either extracted from the surrounding environment or derived independently of the surrounding environment. It is further contemplated that such a sensing device can be uniquely designed so that the container is adapted to generate oxygen which then can be supplied on demand to the enzymatic reaction. In other words, the enzymatic reaction determines the amount of oxygen necessary to convert the analyte to a product which ultimately is sensed. It should be appreciated, however, that the consumption of oxygen as a reactant supplied on demand, by a servo mechanism or other device, to the enzymatic reaction can also function as a measure for the analyte under investigation. It is still further contemplated that, since it has been discovered that the enzymatic reactions utilized by this invention are oxygen limiting, such a sensing device can be constructed so that the container provides a constant supply of oxygen for the enzymatic reaction which is always in excess of the amount needed for the enzymatic reaction.

In a preferred embodiment, the device comprises an enclosed chamber adapted for containing oxygen comprising a wall structure defining a hollow interior and having an external surface wherein at least a portion of the external surface has the enzyme associated therewith for the enzymatic reaction, the wall structure being adapted for allowing molecular oxygen to permeate therethrough to supply molecular oxygen for the enzymatic reaction, an analyte permeable membrane overlying the enzyme and connected to the chamber for allowing the analyte to permeate therethrough to supply the analyte for the enzymatic reaction, and means for sensing the product generated from the enzymatic reaction which functions as a measure of the analyte.

The invention is also directed to novel methods of sensing a product or reactant of an enzymatic reaction between an analyte and an enzyme in presence of oxygen as a measure of the analyte in vivo or in vitro. Such a method comprises providing a gas permeable membrane having opposed sides, providing an enzyme on one side of the membrane for enzymatic reaction with the analyte in presence of molecular oxygen to generate a product, providing a closed container for the molecular oxygen on the opposite side of the membrane to supply molecular oxygen through the membrane for the enzymatic reaction, and sensing the generated product or reactant which functions as a measure of the analyte.

The above features and advantages of the invention will be better understood with reference to the accompanying drawings, detailed description and examples. It will also be understood that the particular devices and methods embodying the invention are exemplary only and not to be regarded as a limitation of the invention.

BRIEF DESCRIPTION OF THE DRAWINGS

Reference is made to the accompanying drawings in which is shown illustrative embodiments of the invention from which its novel features and advantages will be apparent.

FIG. 3b is a depiction of cyclic in vitro polarograms of changing glucose concentrations in undiluted fresh whole goat blood utilizing the same sensor referred to in the description of FIG. 3a.

DETAILED DESCRIPTION OF THE INVENTION

By way of illustrating and providing a better appreciation of the present invention, the following detailed description is given concerning the methods of the invention.

By the term "animal tissue" as used herein, it is meant to include all animal tissues including body fluids and blood.

As used in this specification, "closed container" is meant to refer to a container that is impermeable to substances, such as liquids and cells, that might interfere with the ability of the container or membrane associated with the enzyme to supply oxygen to the enzymatic reaction. By the term "product" generated from the enzymatic reaction, it refers herein to the product produced from such a reaction, like hydrogen peroxide or gluconic acid or pyruvic acid, or products generated from the "product". The term "reactant" is meant to include a substance involved directly or indirectly in the enzymatic reaction, such as oxygen, for instance. It should therefore be appreciated that the biosensor and methods of this invention can sense the products or reactants of the enzymatic reaction, or by-products derived from the generated products, which function as a measure of the analyte.

The term "analyte" refers herein to any material suitable for analysis with polarographic, potentiometric, optical or other techniques. An example of one of many other techniques is conductometric, e.g., glucose is not electrically conductive but gluconic acid can be so detected as a measure of the analyte. Further, hydrogen peroxide can be detected by electron spin resonance, and so forth. Exemplary of analytes that can be detected according to the teachings of this invention include, for instance, glucose and lactate. The product generated, such as hydrogen peroxide, by the enzymatic reaction between an analyte and an enzyme in the presence of oxygen which can be sensed using known standard electrical or optical techniques serves as a measure of the analyte under investigation. For instance, hydrogen peroxide in an electrical system can generate an anodic current when subjected to a sufficient voltage, or, in an optical system, it can react with or be reduced to react with an optical substance to generate chromagens or fluorogens which then can be detected optically.

The present invention is especially directed to devices for sensing hydrogen peroxide generated from an enzyme reaction with glucose or lactate in a liquid sample in the presence of oxygen as a measure of glucose or lactate. Alternatively, oxygen may be sensed as a measure of the analyte. The devices are especially suited for in vivo implantation and detecting such analytes in undiluted, whole blood. The novel biosensors are uniquely designed to provide an independent source of oxygen for the enzymatic reaction to overcome apparent oxygen deficiencies that otherwise arise in the liquid sample under investigation. In other words, it has been found that problems heretofore encountered in enzymatic electrode or optical structures are overcome by the inventive device. The devices of the present invention have been found ideally suitable for use or implantation in low oxygen tension areas, such as the peritoneal cavity, and for measuring glucose therein.

Figure 1:
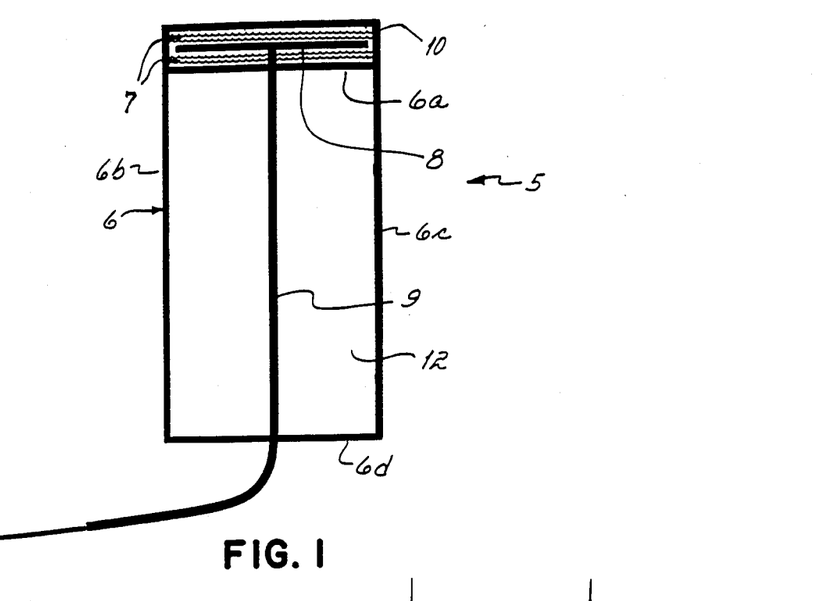
FIG. 1 is a diagrammatic illustration of one form of an electrical device which is illustrative of an embodiment of the invention.

Referring now to FIG. 1, it is a diagrammatic illustration of a typical device of the present invention and illustrates sensor 5 provided with an air space gas pocket 12 on the side of a gas permeable membrane 6a opposite the enzyme which functions as an independent reservoir of oxygen for supplying an enzymatic reaction. More particularly, FIG. 1 depicts a sensor 5 connected to an enclosed container or chamber 6 having top, bottom and opposed sides 6a, 6b, 6c, and 6d, respectively. It should be readily appreciated that, for purposes of the illustration in FIG. 1, top 6a of chamber 6 is the gas permeable membrane. Mounted on outside surface of side 6a of chamber 6 is an enzyme 7 in contact with an anode 8. Preferably, anode 8 is platinum and spread or fanned across the top surface of side 6a of chamber 6. Anode 8 preferably is in the form of a grid or numerous wires (not shown) branching out over top 6a, the membrane, so that the oxygen can diffuse more readily around the anode. Anode 8 which extends into and through chamber 6 is covered in chamber 6 with an insulated wire 9, such as polytetrafluoroethylene commonly referred to under the trademark Teflon. The wire 9 can be situated outside of the chamber. Overlying the enzyme 7 and anode 8 and connected to chamber 6 is an analyte permeable membrane 10. FIG. 1 depicts membrane 10 being sealed to chamber 6 by any suitable means well known to those versed in the art. The analyte permeable membrane can be comprised of any suitable material, such as cellulose. Preferably, membrane 10 is permeable to small molecules, such as glucose and lactate, but impermeable to macromolecules, such as proteins and the like. Exemplary of other suitable membranes that may be employed with the sensors of the present invention are disclosed in Table 1 of Thevenot, D. R.: Problems in Adapting a Glucose-Oxidase ElectroChemical Sensor Into An Implantable Glucose-Sensing Device, *Diabetes Care.* 5(3):184–189 (May-June 1982) in which the entire contents therein is incorporated herein by reference. Chamber 6 is preferably constructed out of material that is gas permeable and liquid impermeable. An ideal material employed having such characteristics is reinforced silastic, such as an organosilicone polymer, like Dow Corning subdermal implant No. 501-1, 0.007 in. thick). To further illustrate the preferred use of silastic to formulate the chamber of this invention, it has been discovered that upon implantation into an animal over a period of time, the chamber remained relatively free of liquid. This is quite a significant discovery especially in view of the fact that silastic is permeable to water vapor. It should be appreciated, however, that other materials having similar characteristics, such as polytetrafluoroethylene commonly referred to under the trademark Teflon, may be employed.

Although not shown in the Figs., it should be appreciated to those in the art that the sensors of the present invention may include a "third" membrane placed over anode 8 to separate enzyme 7 from anode 8. This is commonly referred to as the "sandwich" concept which is well known in the art and exemplified in Clark, L. C., Jr. et al: Rapid Micromeasurement of Lactate in Whole Blood, *Critical Care Medicine.* 2(5):461-464 (May, 1984) and Clark, L. C., Jr, and Duggan, C. A.: Implanted Electroenzymatic Glucose Sensors, *Diabetes Care.* 5(3):174-180 (May-June 1982) which are incorporated in their entirety herein by reference. The "third" membrane may be formed of, for instance, cellulose acetate or the like. The advantages associated with such a membrane are at least twofold. First, such a membrane allows selective diffusion of the enzyme-generated product, such as hydrogen peroxide, to the anode where the peroxide is oxidized resulting in the current which functions as a measure of the enzyme substrate, e.g., glucose or lactate. Secondly, since there can be several potentially interfering substances, such as ascorbic acid and phenolic compounds like acetaminophen, present in the body, the employment of the "third" membrane provides a barrier to such interfering substances reducing the possibility of inaccurate or incorrect measurements. A cellulose acetate membrane has been employed in the art to exclude interfering compounds.

In a further feature of the present invention, the device is designed to extract oxygen from the environment surrounding the chamber. For instance, when the sensor is implanted, the closed container of the present invention preferably is adapted to extract oxygen from the animal tissue located adjacent thereto to provide a constant and self-sufficient supply of oxygen for the enzymatic reaction. As mentioned, the silastic material is ideally suited for this purpose.

In a further feature of the present invention, incorporated into enclosed container or chamber 8 of the device is an oxygen transporting agent, such as a perfluorocarbon or derivative thereof, silicone oils or other organic oxygen solvents. In the case of a perfluorocarbon or derivative thereof, a perfluorocyclocarbon is preferred. Such compositions are well known in the art and an exemplary list of suitable perfluorocarbons and derivatives thereof can be found in my U.S. Pat. Nos. 4,443,480 and 3,911,138 which are incorporated in their entirety herein by reference. The enzyme along with an emulsion comprising a perfluorocarbon or derivative thereof can also be included in chamber 6. In such a case, chamber 6 containing the enzyme should be adapted to permit the enzyme to permeate top 6a therethrough to supply the enzyme for the enzymatic reaction. When the enzyme is incorporated into chamber 6 and top 6a, the membrane, modified for enzyme permeation, enzyme 7 need not be on the outer surface of top 6a, the membrane, as depicted in FIG. 1.

It is further envisaged by the biosensors of the present invention that they may contain audio or visual devices which can serve as a measure of the analyte under investigation and convey to, for instance, an implantee in the case of an implantable sensor, such information via audio or visual means, respectively. In the case of audio devices, such devices may be programmed to provide an audio sound all day or at certain times of the day which would reflect the concentration of, for example, glucose in the blood. Radio telemetry devices can be employed. With respect to visual devices, these devices would be programmed to provide all day or intermittently, for instance, a light in which the intensity thereof would serve as a function of the analyte. The use of such audio or visual techniques are well known to those skilled in the art and can be adapted to be used in connection with the present invention for the purposes described above.

When an electrical sensor is employed, the voltage applied may be fixed, switched, cycled or pulsed. When the voltage applied is fixed, it may be applied in the range of about 0.5 to about 1.0 positive or negative volts for sensing the product generated, such as hydrogen peroxide, to detect the analyte or for detecting oxygen, respectively. Preferably, the fixed voltage should be at about +0.6 or −0.6 volts for measuring the analyte or oxygen. When the voltage applied is switched, i.e., switched between anodic and cathodic voltages over time for generating anodic and cathodic currents, respectively, it may be applied in a range of up to about 1.3 positive or negative volts for detecting the analyte or oxygen, respectively. Preferably, the switched voltage should be at about −0.6 volts when detecting oxygen and +0.6 volts when detecting the analyte. Such methods for detecting both oxygen and the analyte have been admirably described in my presently pending U.S. application, Ser. No. 650,344 and the entire contents of that application is incorporated herein by reference. When the voltage applied is cycled, the voltage may be applied in a loop starting, for example, at positive going to negative and back to positive in a range of from about +0.5 to −0.5 to +0.5 volts, and preferably from about +0.6 to −0.6 to +0.6 volts. In other words, the voltage applied is cycled over the appropriate range. The advantages to cycling the voltage are numerous. For instance, by cycling the applied voltage, it permits the molecular oxygen to be examined almost simultaneously with the analyte under investigation to ensure that a sufficient supply of oxygen is available for the reaction. Additionally, it has been learned that the cycling technique provides for a cleaner electrode, e.g., it reduces the amount of plating presently encountered on a platinum electrode. It also has been learned that cycling the voltage neutralizes the environment immediately surrounding the sensor. This is particularly advantageous since an anodic current generates hydrogen ions and a cathodic current generates hydroxyl ions. When the voltage is pulsed, the voltage is turned on intermittently in brief intervals, such as for example about ten seconds to about sixty seconds every five minutes or longer, for purposes of sensing a generated product, like hydrogen peroxide, after a steady state has been achieved around the sensor. It is believed, that the use of the pulsing technique results in higher currents and better measurements because of the steady state achieved. Such pulsing techniques are described in U.S. Pat. No. 4,464,230 and the entire contents thereof is incorporated herein by reference.

In a further aspect of the invention, a two electrode or three electrode system may be utilized. Although such systems are not shown, these systems are well known in the art. Generally speaking, the two electrode system is suitable for measuring analytes in aqueous solutions having high electrical conductivity whereas three electrode systems are suitable for measuring analytes in solution with low conductivity. In either a two or three electrode system, it should be appreciated that the "reference" and "counter" electrodes may be located remote from, near or included as part of the sensor. When the electrodes are included as part of the sensor, which is the preferred form, it is most preferred that the electrodes all be located on the same side of the membrane especially when analyzing analytes in low conductivity samples.

In addition to providing an electrical device for sensing hydrogen peroxide or a product produced therefrom, the present invention contemplates providing an optical sensor utilizing, for example, a dye in connection with monochromatic, dichromatic or multiple chromatic light which can be transmitted through an optical fiber and the light spectrum received with known instrumentation to reveal the analyte concentration of a liquid sample under investigation. In using a chromatic light sensor, the dye can be, for example, located on membrane 6a in contact with enzyme 7 for reacting with hydrogen peroxide or a product generated therefrom to generate a color which can be optically sensed and which functions as a measure of the analyte under investigation. In addition, as a result of enzymatic reactions, fluorescence and phosphorescence can occur. Hence, by a suitable device containing an enzyme, a fluorescent or phosphorescent dye and the photoactivating product, i.e, hydrogen peroxide or a product derived therefrom, generated from the enzymatic reaction, one can detect an analyte concentration by measuring the amount of light emitted through the fiber optic by the fluorescence or phosphorescent reaction between the hydrogen peroxide or product derived therefrom and the fluorescent or phosphorescent dye. Such dyes are known which fluoresce in presence of hydrogen peroxide. Further, the color of phenol red is pH dependent. It would change (red to yellow) as more gluconate is produced from glucose, and such a method could also be used.

In accordance with a further aspect of this invention and as aforementioned, the devices may be utilized in vitro or in vivo. When utilizing the device in vitro, the measurement should preferably be made in, for example, a suitable amount of a magnetically stirred buffer or whole blood in, for instance, a glass chamber jacketed with water circulating at about 37°. Exemplary of buffers suitable for use include phosphate buffers, such as Gomori buffer which is well known and described in the art. A glucose measurement can be made directly in whole blood on the finger, from a finger cut, using a temperature compensated precalibrated sensor.

With respect to implantation, i.e., in vivo, of the devices in an animal including a human, any known technique not inconsistent with this invention may be employed. Exemplary of such a technique is described in Clark, L. C. et al: Theoretical and Practical Basis for Implantable Glucose Sensors with Special Reference to the Peritoneum, Proceedings of the Symposium on Biosensors. Los Angeles, Calif. A. R. Potvin and Mr. Neuman (Eds.) *Institute of Electrical and Electronics Engineering (IEEE)*. New York, N.Y. pp. 69-74 (Sept. 15-17, 1984) and Clark, L. C. and Duggan, A.: Implanted Electroenzymatic Glucose Sensor, *Diabetes Care.* 5(3):174-180 (May-June 1982) which both are incorporated herein by reference in their entirety. As to the site of implantation, the devices may be implanted in both blood and non-blood sites. Exemplary of non-blood sites include subcutaneous, intramuscular, epihepatic, intraperitoneal and brain sites, and most preferably intraperitoneal sites. With respect to the intraperitoneal sites, the sensor may be implanted in, on or near, but not limited to, the pancreas, liver, peritoneum, stomach, or intestines. Of course, it is contemplated herein, that when such devices are implanted, they can be adapted for use with insulin pumps or other related devices in vivo or in vitro in connection with diabetic patients. Exemplary of such use can be found in Albisser, A. M.: Insulin Delivery Systems: Do They Need a Glucose Sensor, *Diabetes Care.* 5(3):166-173 (May-June 1982) which is also incorporated in its entirety herein by reference.

With respect to enzyme 7, it is preferably located on the outer surface of side 6a of a chamber 6 in contact with a platinum anode 8. The enzymes are preferably immobilized and stabilized thereon via glutaraldehyde treatment well known in the art. For example, after assembly of a sensor in accordance with the teachings of this invention, it is placed in the vapor of glutaraldehyde in a glass chamber overnight. The vapor is generated by a layer of 25% glutaraldehyde in the bottom of the chamber. This treatment, which is conducted at room temperature, serves to insolubilize and/or stabilize the enzyme, such as glucose oxidase, and to sterilize the sensor. Following treatment, it preferably is stored in 70 percent ethanol in the cold, until used. It has been found that traces of residual glutaraldehyde can be detected by cyclic voltammetry. In this way, it is possible to be sure that the excess glutaraldehyde has been removed. Other sensitive tests for traces of glutaraldehyde, such as those used after re-use sterilization of clinical dialyzers, are used occasionally. When glucose is being measured, glucose oxidase derived from sources, such as *Penicillin notatum* or *Aspergillus niger*, may be used.

In view of the above enzymatic reaction, it is obvious that a number of oxygen oxidoreductase in addition to glucose oxidase and lactate oxidase can be used in order to detect and measure numerous analytes in vivo or in vitro. The following table is an exemplary listing of many of the enzymes, their identifying number, source and typical analytes with which they may react for measuring in accordance with the principles of this invention.

TABLE

| Enzyme | Number | Source | Typical Substrates |
| --- | --- | --- | --- |
| Glycollate oxidase | 1.1.3.1 | spinach<br>rat liver | glycollate<br>L-lactate<br>D-lactate<br>(+)-mandalate |
| Lactate oxidase | 1.1.3.2 | *M. phlei* | L-lactate |
| Glucose oxidase | 1.1.3.4 | *Aspergillus niger*<br>*Penicillium amagasakienses*<br>honey (bee)<br>*Penicillium notatum* | β-D-glucose<br>2-dioxy-D-glucose<br>6-dioxy-6-fluoro-D-glucose<br>6-methyl-D-glucose |
| Hexose oxidase | 1.1.3.5 | | β-D-glucose<br>D-galactose<br>D-mannose |
| L-Gulonolactone oxidase | 1.1.3.8 | rat liver | L-gulono-λ-lactone |

TABLE-continued

| Enzyme | Number | Source | Typical Substrates |
|---|---|---|---|
| Galactose oxidase | 1.1.3.9 | *Dactylium dendroides* *Polyporus circinatus* | L-galactonolactono D-manonolactone D-altronolactone D-galactose stachyose lactose |
| L-2-Hydroxyacid oxidase | 1.1.3.a | hog renal cortex | L-2-hydroxyacid |
| Aldehyde oxidase | 1.2.3.1 | rabbit liver pig liver | formaldehyde acetaldehyde |
| Xanthine oxidase | 1.2.3.2 | bovine milk porcine liver | purine hypoxanthine benzaldehyde xanthine |
| Pyruvate oxidase | 1.2.3.3 | | puruvate requires thiamine phosphate |
| Oxalate oxidase | 1.2.3.4 | | oxalate |
| Dihydro-orotate-dehydrogenase | 1.3.3.1 | *Zymobacterium oroticum* | L-4, 5-dihydro-orotate NAD |
| D-Aspartate oxidase | 1.4.3.1 | rabbit kidney | D-aspartate D-glutamate |
| L-Amino-acid oxidase | 1.4.3.2 | diamond rattlesnake cotton mouth moccasin rat kidney | L-methionine L-phenylalanine 2-hydroxy acids L-lactate |
| D-Amino acid oxidase | 1.4.3.3 | hog kidney | D-alanine D-valine D-proline |
| Monoamine oxidase | 1.4.3.4 | beef plasma placenta | monoamine benzlamine octylamine |
| Pyridoxamine phosphate oxidase | 1.4.3.5 | rabbit liver | pyridoxamine phosphate |
| Diamine oxidase | 1.4.3.6 | bovine plasma pea seedlings procine plasma | diamines spermidine tyramine |
| Sarcosine oxidase | 1.5.3.1 | *Macaca mulatta* rat liver metochondria | sarcosine |
| N—Methyl-L-amino acid oxidase | 1.5.3.2 | | N—methyl-L-amino acids |
| Spermine oxidase | 1.5.3.3 | *Neisseria perflava* *Serratia marcescens* | spermine spermidine |
| Nitroethane oxidase | 1.7.3.1 | | nitroethane aliphatic nitro compounds |
| Urate oxidase | 1.7.3.3 | hog liver ox kidney | urate |
| Sulfite oxidase | 1.8.3.1 | beef liver | sulfite |
| Alcohol oxidase | | Basidiomycetes | ethanol and methanol |
| Carbohydrate oxidase | | Basidiomycetes *Polyporus obtusus* | D-glucose D-glucopyranose D-xylopyranose l-sorbose α-D-gluconolactone |
| NADH oxidase | | beef heart mitochondria | NADH |
| Malate oxidase | 1.1.3.2 | | L-malate |
| Cholesterol oxidase | 1.1.3.6 | | cholesterol |
| N—Acetylindoxyl oxidase | 1.7.3.2 | | N—acetylindoxyl |
| Thiol oxidase | 1.8.3.2 | | R: CR-SH |
| Ascorbate oxidase | 1.10.3.3 | squash | L-ascorbate |

It is also contemplated herein to incorporate into, on or near the enclosed chamber 6, an electrolytic device or means for generating oxygen independent of the environment adjacent the device for independently generating or replenishing the reservoir of oxygen in the chamber. Such a device or means may be a small battery (not shown) attached on, near or inside chamber 6 for generating oxygen inside the chamber, or an oxygen generating cell (not depicted) comprising phosphoric acid which becomes exposed to electrolyzed water from dissolved water vapor inside chamber 6 to produce oxygen. Oxygen from the electrolysis diffuses toward the sensor while hydrogen is preferred to diffuse away from the sensor towards the body; arrangeable by design of the electrolyte cell in the drum.

An electroenzymatic glucose sensor and an exemplary use thereof in accordance with the present invention will now be further illustrated by reference to the following examples.

EXAMPLE 1

A typical electroenzymatic sensor in accordance with this invention has been prepared as follows.

The drum was prepared from a piece of Dow Corning silastic tubing 0.1875 inches I.D.×0.3125 inches O.D. A piece of about one centimeter was cut from this tubing and then on each end of the tubing was cemented to silastic sheeting using Dow Corning silastic medical adhesive silicone type catalog No. 891 glue. The silastic sheeting or membrane was made by the Dow Corning Company and a one centimeter diameter circle of 0.010 inch thick material was cut. The drum head was placed on both ends of the silastic tubing to form an enclosed drum. The wire used was MedWire Corp. platinum-iridium consisting of 9 strands of 0.0011 inch wire insulated with Teflon. A distance of about five millimeters of this wire's insulation was cut exposing the 9 strands of wire which were spread out across the surface of the drum. The wire was then put in 0.025 inches I.D.×0.047 inches O.D. silastic tubing and fastened to the edge of the tubing using silk thread. Then over the end of the electrode, where the platinum iridium wire had been spread out, was placed a piece of regenerated cellulose membrane which was porous to glucose. The type found most useful was that called Spectropor and this was tubing made for dialysis and was made by the Viscos process. When inflated, dialyzer tubing obtained from Arthur H. Thomas Co., Philadelphia, PA which has catalog No. 3787-F45, one and a quarter inch in diameter was used. Such tubing was merely used as a membrane. The tubing was soaked in water before applying and it was applied after the glucose oxidase was coated on the platinum wires on the end of the silastic drum. The membrane was stretched over the edge and then tied in place with many turns of silk thread. An important part of the process was to coat the 9 strands of platinum iridium wire with the enzyme glucose oxidase which was obtained from the Sigma Chemical Co., St. Louis, MO as a frozen powder identified by catalog No. G-2133 which was a crystalline glucose oxidase, a bright yellow powder, mixed in equal quantity with gluconic acid as a preservative. Glucose oxidase, where the gluconic acid had been removed by dialysis and freeze dried, may also be used. The glucose oxidase powder was simply dissolved in water to make a concentrated mixture and then spread over the wire. Then, as mentioned above, the cellulose membrane was pulled down over the enzyme coated platinum iridium wire. Thereafter, the entire sensor was put in the vapor phase created from about 25% aqueous glutaraldehyde overnight in a glass chamber wherein the glutaraldehyde was poured in the bottom of this closed glass chamber. The sensor, after treatment with the glutaraldehyde vapor which served to immobilize and insolubilize the enzyme, was removed and tested in a stirred cuvet containing phosphate buffered 7.4 and equilibrated or bubbled with air. The measurements were made at a temperature of about 40° C. Such an electroenzymatic electrode was suitable as an implantable electrode or for use with undiluted, whole blood as a dipping electrode. In the implanted sensor following this procedure of calibration where increasing amounts of glucose were added to the stirred buffer, the glucose sensor was stored in 70% alcohol in the cold in the refrigerator until implanted in an animal.

EXAMPLE 2

Figure 2:
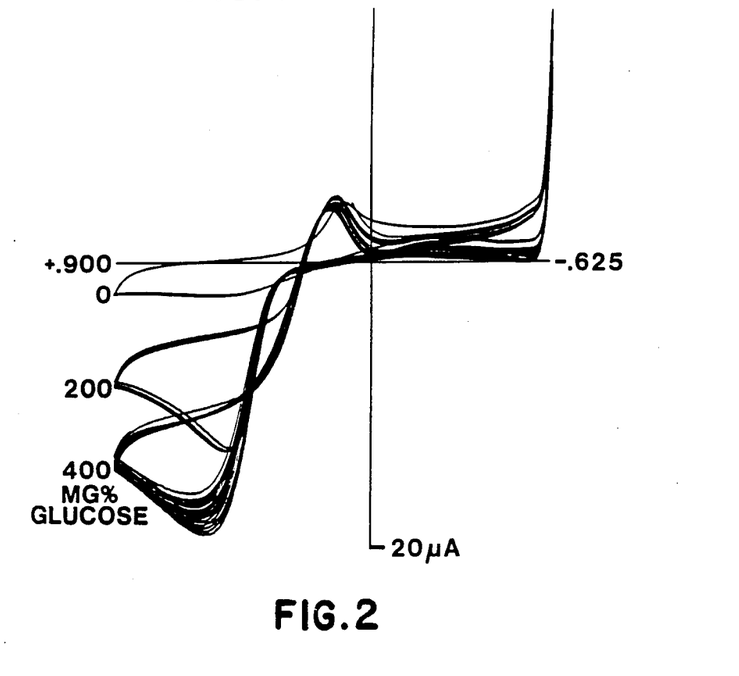
FIG. 2 is a depiction of generated cyclic in vitro polarograms of changing glucose concentrations in a liquid sample, e.g., Gomori buffer, void of oxygen utilizing the electrical device described in Example 1.

In FIG. 2 are shown cyclic in vitro polarograms generated by the electroenzymatic glucose sensor described in Example 1 which measured changing glucose concentrations in a thermostated cuvet which contained Gomori buffer. The $pO_2$ of the Gomori buffer was first brought near zero by bubbling nitrogen therethrough. Then glucose was added, first to make it 200 mg %, then 400 mg %. The current response (lower left quadrant) shows that the oxygen supply (upper right quadrant) was adequate and had to come from inside the closed container of the sensor.

EXAMPLE 3

Figure 3A:
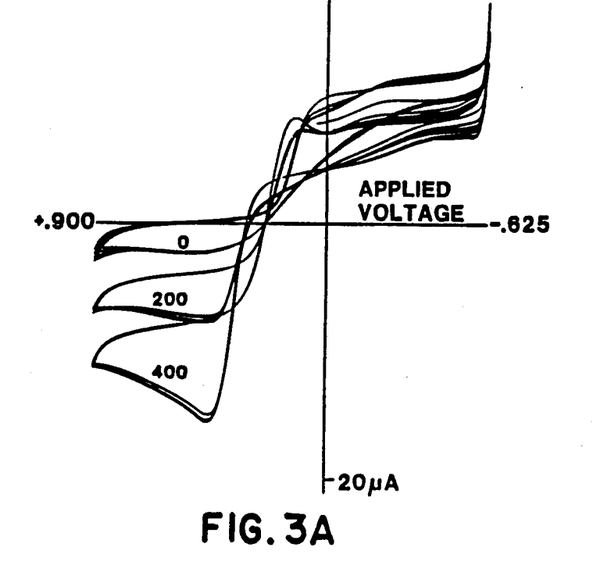
FIG. 3a is a depiction of generated cyclic in vitro polarograms of changing glucose concentrations in a liquid sample, e.g., Gomori buffer, utilizing an electroenzymatic glucose sensor of the present invention.

In FIGS. 3a and 3b exemplify cyclic in vitro polarograms that can be generated with an electroenzymatic sensor of this invention reflecting changing glucose concentrations in a thermostated cuvet containing Gomori buffer. The $pO_2$ of the Gomori buffer is first brought near zero by bubbling nitrogen therethrough. The glucose is then added, first to make it 200 mg %, then 400 mg % as illustrated in FIG. 3a.

Figure 3B:
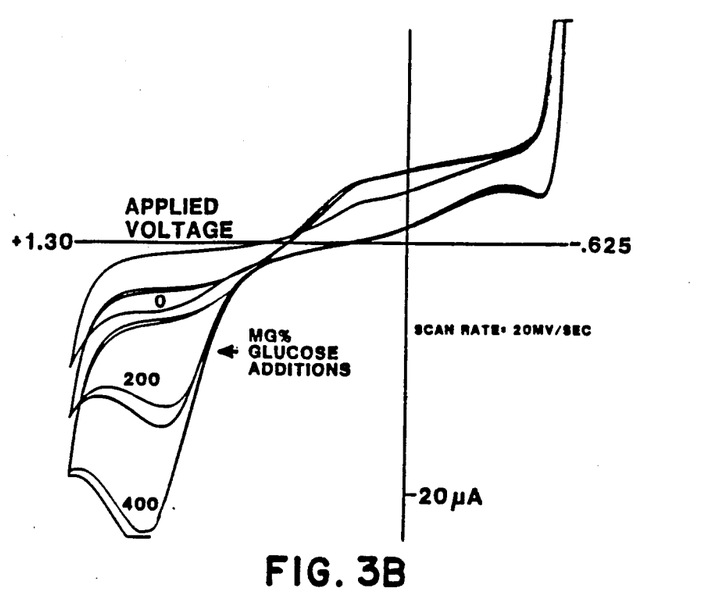

Thereafter, the same device can be used to detect changing glucose concentrations in undiluted, fresh whole goat blood as shown in FIG. 3b. It should be noted that in both FIGS. 3a and 3b, the $pO_2$ does not decrease (upper right quadrant) as the glucose is increased. Thus, the current responses (lower left quadrant) show that the oxygen supply (upper right quadrant) is adequate in both the Gomori buffer solution and the undiluted, fresh whole goat's blood, and the oxygen comes from the chamber of the sensor at least in the case of the Gomori buffer, as depicted in FIGS. 3a and 3b.

The present invention may, of course, be carried out in other specific ways than those herein set forth without departing from the spirit and essential characteristics of the invention. The present embodiments are, therefore, to be considered in all respects as illustrative and not restrictive and any changes coming within the meaning and equivalency range of the appended claims are to be embraced therein.

What is claimed is:

1. A device for sensing a product or reactant of an enzyme reaction with an analyte as a measure of the analyte comprising
   a gas and enzyme permeable membrane having opposed sides,
   an enzyme on one side of said membrane for permeation through said membrane and enzymatic reaction with the analyte in presence of oxygen to provide the product or reactant,
   a closed container for containing oxygen on the enzyme side of said membrane to supply oxygen through said membrane for the enzymatic reaction, and
   means for sensing the product or reactant as a function of the analyte.

2. A device of claim 1 further comprising an analyte permeable membrane overlying said enzyme permeable membrane for allowing the analyte to permeate therethrough to supply the analyte for the enzymatic reaction.

3. A device of claim 2 wherein said analyte permeable membrane comprises cellulose.

4. A device of claim 1 wherein said sensing means is an electrical sensor or an optical sensor.

5. The device of claim 4 wherein said sensor is adapted to sense hydrogen peroxide or as a measure of the analyte.

6. A device of claim 4 wherein said electrical sensor is a platinum anode in contact with said enzyme for electrolytically sensing the product or reactant from the enzymatic reaction.

7. A device of claim 4 wherein said optical sensor comprises an optical substance in contact with said enzyme for optical reaction with the product or reactant from the enzymatic reaction and a fiber optic for sensing the optical reaction which functions as a measure of the analyte.

8. A device of claim 7 wherein said optical substance is selected from the class consisting of a chromatic dye and a fluorescent dye.

9. A device of claim 1 wherein said membrane comprises a organosilicone polymer.

10. A device of claim 1 wherein said enzyme is selected from the class consisting of oxygen oxidoreductases.

11. A device of claim 1 wherein said closed container has a wall structure defining a hollow interior adapted for containing oxygen wherein said gas permeable membrane comprises at least a portion of the wall structure.

12. A device of claim 11 wherein said container is gas permeable and liquid impermeable.

13. A device of claim 11 wherein said container is permeable to oxygen.

14. A device of claim 13 wherein said container comprises an organo-silicone polymer.

15. A device of claim 1 wherein said container is adapted to extract oxygen from animal tissue adjacent thereto.

16. A device of claim 1 wherein said container comprises additional means for generating oxygen for supplying oxygen through said membrane for the enzymatic reaction.

17. A device of claim 1 wherein said container contains an oxygen transport substance.

18. A device of claim 17 wherein said oxygen transport substance is a perfluorocarbon or derivative thereof.

19. A device of claim 18 wherein said perfluorocarbon or derivative thereof is a perfluorocyclocarbon.

20. A device of claim 1 wherein said container contains said enzyme and an emulsion comprising a perfluorocarbon or derivative thereof wherein said membrane is adapted to allow said enzyme present in said container to permeate therethrough to supply said enzyme for the enzymatic reaction.

21. A device of claim 20 wherein said perfluorocarbon or derivative thereof is a perfluorocyclocarbon.

22. A device of claim 20 wherein said enzyme is selected from the class consisting of oxygen oxidoreductases.

23. A device for sensing a product or reactant of an enzyme reaction with an analyte in presence of oxygen which functions as a measure of the analyte comprising
an enclosed chamber adapted for containing oxygen and enzyme comprising a wall structure defining a hollow interior, a portion of the wall structure being adapted for allowing oxygen and enzyme to permeate therethrough to supply oxygen and enzyme for the enzymatic reaction,
an analyte permeable membrane overlying said portion of the wall structure and connected to said chamber for allowing the analyte to permeate therethrough to supply the analyte for the enzymatic reaction, and
means for sensing the product or reactant of the enzymatic reaction which functions as a measure of the analyte.

24. A device of claim 23 wherein said sensing means is an electrical means or an optical means.

25. The device of claim 23 wherein said sensor is adapted to sense hydrogen peroxide as a measure of the analyte.

26. device of claim 24 wherein said electrical means is a platinum anode in contact with the enzyme for electrolytically sensing the product or reactant of the enzymatic reaction.

27. A device of claim 23 wherein said chamber is adapted to extract oxygen from animal tissue adjacent thereto.

28. A device of claim 23 wherein said chamber includes additional means for generating oxygen for permeating through the wall structure to supply oxygen for the enzymatic reaction.

* * * * *

UNITED STATES PATENT AND TRADEMARK OFFICE
CERTIFICATE OF CORRECTION

PATENT NO. : 4,721,677

DATED : January 26, 1988

INVENTOR(S) : Leland C. Clark, Jr.

Page 1 of 3

It is certified that error appears in the above-identified patent and that said Letters Patent is hereby corrected as shown below:

The title page should be deleted to appear as per attached title page.

Col. 1, line 15 "wer" should be --were--

Col. 1, line 27 "3,913,386" should be --2,913,386--

Col. 6, line 50 "ElectroChemical" should be --Electrochemical--

Col. 7, line 8 "2(5):461-464" should be --12(5):461-464--

Col. 7, line 51 "enzyme should" should be --enzyme 7A should--

Col. 10, line 47 "oxidoreductase in" should be --oxidoreductase enzymes in--

In the TABLE at Columns 11 and 12, under the heading "Typical Substrates", 7th line from the bottom" "α-D-gluconolactone" should be --δ-D-gluconolactone--

Signed and Sealed this

Twenty-first Day of May, 1991

Attest:

HARRY F. MANBECK, JR.

Attesting Officer

Commissioner of Patents and Trademarks

United States Patent [19]

Clark, Jr.

[11] Patent Number: 4,721,677
[45] Date of Patent: Jan. 26, 1988

[54] IMPLANTABLE GAS-CONTAINING BIOSENSOR AND METHOD FOR MEASURING AN ANALYTE SUCH AS GLUCOSE

[75] Inventor: Leland C. Clark, Jr., Cincinnati, Ohio
[73] Assignee: Children's Hospital Medical Center, Cincinnati, Ohio
[21] Appl. No.: 47,013
[22] Filed: May 7, 1987

Related U.S. Application Data

[62] Division of Ser. No. 777,234, Sep. 18, 1985, Pat. No. 4,680,268.

[51] Int. Cl.$^4$ .............................................. C12M 1/34
[52] U.S. Cl. ..................................... 435/291; 128/635; 204/403; 204/415; 435/288
[58] Field of Search ................. 128/635; 204/403, 415; 435/288, 291, 808, 817

[56] References Cited

U.S. PATENT DOCUMENTS

| | | | |
|---|---|---|---|
| 2,913,386 | 11/1959 | Clark, Jr. | 204/415 |
| 3,380,905 | 4/1968 | Clark, Jr. | 204/415 |
| 3,539,455 | 11/1970 | Clark, Jr. | 204/1 T |
| 3,577,332 | 5/1971 | Porter et al. | 204/408 |
| 3,591,480 | 7/1971 | Neff et al. | 435/288 X |
| 3,911,138 | 10/1975 | Clark, Jr. | 514/746 |
| 3,992,158 | 11/1976 | Przybylowicz et al. | 422/57 |
| 4,040,908 | 8/1977 | Clark, Jr. | 435/11 |
| 4,151,845 | 5/1979 | Clamens | 128/214 E |
| 4,240,889 | 12/1980 | Yoda et al. | 435/288 X |
| 4,245,634 | 1/1981 | Albisser et al. | 128/213 R |
| 4,313,439 | 2/1982 | Babb et al. | 128/214 F |
| 4,368,737 | 1/1983 | Ash | 604/175 |
| 4,374,013 | 2/1983 | Enfors | 204/1 T X |
| 4,378,016 | 3/1983 | Loeb | 128/260 |
| 4,388,166 | 6/1983 | Suzuki et al. | 204/403 |
| 4,402,694 | 9/1983 | Ash et al. | 604/891 |
| 4,403,984 | 9/1983 | Ash et al. | 604/50 |
| 4,443,480 | 4/1984 | Clark, Jr. | 424/352 |
| 4,458,686 | 7/1984 | Clark, Jr. | 128/635 |
| 4,464,230 | 8/1984 | Langdon | 204/1 T |
| 4,484,987 | 11/1984 | Gough | 204/1 T |

OTHER PUBLICATIONS

L. C. Clark, Jr.: Electrode Systems for Continuous Monitoring in Cardiovascular Surgery, Annals New York Academy of Sciences, vol. 102, Article 1, pp. 29–45, Oct. 31, 1962.

L. C. Clark, Jr. et al: Rapid Electroenzymatic Measurement of Lactate in Microsamples of Spinal Fluid, Clinical Biochemistry, vol. 17, Oct. 1984.

S. Kaplan et al: Intravascular Polarographic and Potentiometric Electrodes, Intravascular Catheterization, Chapter 10, pp. 583–605.

M. Shichiri et al: Glycaemic Control in Pancreatectomized Dogs with a Wearable Artificial Endocrine Pancreas, Diabetologia (1983) 24: 179–184.

L. C. Clark, Jr. et al: Continuous Recording of Blood Oxygen Tensions by Polarography, J. Appl. Physiol., 6(3), 189–193 (1953).

(List continued on next page.)

Primary Examiner—Samuel Scott
Assistant Examiner—Allen J. Flanigan
Attorney, Agent, or Firm—Wood, Herron & Evans

[57] ABSTRACT

The present invention relates to a novel implantable biosensor and method for sensing products, such as hydrogen peroxide, generated from an enzymatic reaction between an analyte, like glucose, and an enzyme in the presence of oxygen. The novel implantable biosensor is uniquely equipped with an enclosed chamber for containing oxygen and can be adapted for extracting oxygen from animal tissue adjacent the container. The reservoir of oxygen contained in the enclosed chamber is supplied to the enzymatic reaction from both sides of a membrane. The enclosed chamber is uniquely designed to be impermeable to substances, like liquid and cells, that possibly can interfere with the supply of the oxygen permeating through the membrane to the enzymatic reaction. Also, the implantable biosensor is designed to optically or electrically sense products generated from the enzymatic reaction which serve as a function of the analyte.

28 Claims, 4 Drawing Figures

UNITED STATES PATENT AND TRADEMARK OFFICE
CERTIFICATE OF CORRECTION

PATENT NO. : 4,721,677

DATED : January 26, 1988

INVENTOR(S) : Leland C. Clark, Jr.

Page 3 of 3

It is certified that error appears in the above-identified patent and that said Letters Patent is hereby corrected as shown below:

FIG. 1 should be corrected as shown herein below to include reference to enzyme 7A

FIG. 1